United States Patent [19]

Kirino et al.

[11] 4,394,379

[45] Jul. 19, 1983

[54] AMIDE PHOSPHOROTHIOLATE DERIVATIVES AND THEIR USE AS PESTICIDES

[75] Inventors: Osamu Kirino, Ashiya; Masachika Hirano, Ibaraki; Hisami Takeda; Toshiro Kato, both of Takarazuka, all of Japan

[73] Assignee: Sumitomo Chemical Company, Limited, Osaka, Japan

[21] Appl. No.: 113,133

[22] Filed: Jan. 17, 1980

Related U.S. Application Data

[63] Continuation-in-part of Ser. No. 58,565, Jul. 18, 1979, abandoned.

[30] Foreign Application Priority Data

Jul. 21, 1978 [JP] Japan .................................. 53/89712

[51] Int. Cl.³ ...................... A01N 57/14; C07F 9/165; C07F 9/40
[52] U.S. Cl. ..................................... 424/211; 260/942
[58] Field of Search ......................... 260/942; 424/211

[56] References Cited

U.S. PATENT DOCUMENTS 3,517,089  6/1970  Newallis et al. ..................... 260/942
4,023,956  5/1977  Yoshida et al. ..................... 424/211

Primary Examiner—Anton H. Sutto
Attorney, Agent, or Firm—Wenderoth, Lind & Ponack

[57] ABSTRACT

Amide phosphorothiolate derivatives of the formula,

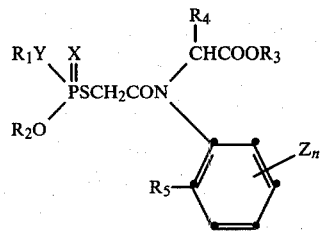

wherein X is an oxygen or sulfur atom, Y is an oxygen or sulfur atom or imino group, $R_1$ and $R_2$, which may be the same or different, are each a $C_1$–$C_3$ alkyl group, $R_3$ is a $C_1$–$C_4$ alkyl group, $R_4$ is a hydrogen atom or methyl group, $R_5$ is a $C_1$–$C_3$ alkyl, methoxy or ethoxy group, Z is a hydrogen atom, a methyl group or chlorine atom and n is 1 or 2, a process for producing said derivatives characterized by reacting the salt of thiophosphoric ester represented by the formula,

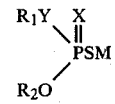

wherein X, Y, $R_1$ and $R_2$ are as defined above and M is a sodium or potassium atom or ammonium group, with a haloacetamide derivative of the formula,

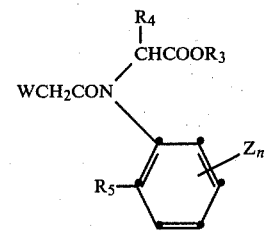

wherein $R_3$, $R_4$, $R_5$, Z and n are as defined above and W is a halogen atom, and a combined insecticide, acaricide, nematocide and/or fungicide containing said derivatives as an active ingredient.

13 Claims, No Drawings

AMIDE PHOSPHOROTHIOLATE DERIVATIVES AND THEIR USE AS PESTICIDES

This application is a continuation-in-part of Ser. No. 58,565 filed on July 18, 1979, now abandoned.

The present invention relates to novel amide phosphorothiolate derivatives, their production and a combined insecticide, acaricide, nematocide and/or fungicide containing said derivatives as an active ingredient. More particularly, it relates to (1) amide phosphorothiolate derivatives of the formula (I),

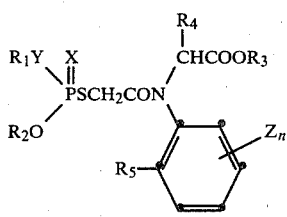

wherein X is an oxygen or sulfur atom, Y is an oxygen or sulfur atom or imino group, $R_1$ and $R_2$, which may be the same or different, are each a $C_1$-$C_3$ alkyl group, $R_3$ is a $C_1$-$C_4$ alkyl group, $R_4$ is a hydrogen atom or methyl group, $R_5$ is a $C_1$-$C_3$ alkyl, methoxy or ethoxy group, Z is a hydrogen atom, a methyl group or chlorine atom and n is 1 or 2, (2) a process for producing said derivatives of the formula (I), characterized by reacting the salt of thiophosphoric ester represented by the formula (II),

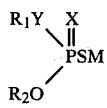

wherein X, Y, $R_1$ and $R_2$ are as defined above and M is a sodium or potassium atom or ammonium group, with a haloacetamide derivative of the formula (III),

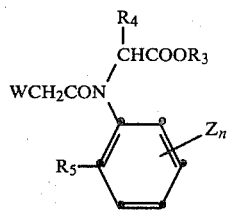

wherein $R_3$, $R_4$, $R_5$, Z and n are as defined above and W is a halogen atom (Cl, Br, I), and (3) a combined insecticide, acaricide, nematocide and/or fungicide characterized by containing said derivatives of the formula (I) as an active ingredient.

A smaller group of compounds within the scope of formula (I) is that wherein X is a sulfur atom, Y is an oxygen atom, $R_1$ and $R_2$, which may be the same or different, are each a methyl or ethyl group, $R_3$ is a methyl or ethyl group, $R_4$ is a hydrogen atom or methyl group, $R_5$ is a methyl, ethyl, methoxy or ethoxy group, Z is a hydrogen atom or a methyl group and n is 1 or 2.

Although compounds having a somewhat similar structure to the present compounds of the formula (I) are well known in Japanese Patent Publication (unexamined) No. 37624/1978 and Canadian Pat. No. 822,142 (the latter corresponding to U.S. Pat. No. 3,517,089), it is apparent from the examples described hereinafter that the present invention was completed on the basis of independent novel information.

The compounds of the present invention have a very strong activity against harmful insects belonging to Hemiptera, Diptera or Lepidoptera as well as plant-parasitic mites and nematodes, so that they are used very advantageously for controlling insects harmful to trees in woods or forests, and harmful unsanitary insects. Particularly, they have a very high lethal effect against rice stem borers, houseflies and mites.

Further, the compounds of the present invention have a very strong protective activity on various diseases so that they are also very useful as fungicides in the field of agriculture. Particularly, they are useful for controlling diseases caused by Phycomycetes such as late blight of potato (*Phytophthora infestans*), late blight of tomato (*Phytophthora infestans*), downy mildew of cucumber (*Pseudoperonospora cubensis*), downy mildew of grape (*Plasmopara viticola*), club-root of chinese cabbage (*Plasmodiophora brassicae*) and the like. The compounds of the present invention are superior to the conventional fungicides in that they have not only a preventive effect but also a curative effect against these diseases.

The present invention relates to (1) the amide phosphorothiolate derivatives of the formula (I), (2) their production and (3) a combined insecticide, acaricide, nematocide and/or fungicide characterized by containing said derivatives of the formula (I) as an active ingredient.

In (2), the salt of thiophosphoric ester represented by the formula (II) can easily be obtained by the method disclosed, for example, in "Methoden der Organischen Chemie," 587 (1964). The haloacetamide derivatives of the formula (III) can easily be synthesized by the method disclosed, for example, in Japanese Patent Publication (unexamined) No. 71138/1974.

In carrying out (2), in general, the salt of thiophosphoric ester represented by the formula (II) is dissolved or suspended in a suitable solvent and allowed to react with a haloacetamide derivative of the formula (III) with stirring under heating or cooling if necessary. The solvent includes for example ketones (e.g. acetone, methyl ethyl ketone, diethyl ketone, methyl isobutyl ketone), nitriles (e.g. acetonitrile, propionitrile), ethers (e.g. tetrahydrofuran, dioxane), aliphatic or aromatic hydrocarbons (e.g. petroleum ether, benzene, toluene, xylene), halogenated hydrocarbons (e.g. methylene chloride, chloroform, chlorobenzene), esters (e.g. ethyl acetate), alcohols (e.g. methyl alcohol, ethyl alcohol, propyl alcohol) and water. Of these solvents, acetone is particularly preferred.

The molar ratio of the salt of thiophosphoric ester (II) to haloacetamide (III) is optical, but preferably it is 1-1.3 to 1. The addition of the compounds (II) and (III) may be the reverse of the foregoing order. The reaction temperature is optional in a range between the freezing point and boiling point of solvent used, but preferably it is in a range of 5° to 50° C. The reaction time is optional, provided that it is sufficient to produce the compounds (I). The compounds (I) are isolated in a high purity and high yield by the usual methods, for example, by removing the produced inorganic salt by filtration or washing with water, followed by removal of the solvent under reduced pressure. The isolated compounds may further be purified, for example, by column chromatography on silica gel.

In producing the combined insecticide, acaricide, nematocide and/or fungicide of the present compounds (I), the compounds may be formulated into optional preparation forms using the common carriers or diluents for agricultural chemicals, like the conventional organic phosphates, according to the methods well known to those skilled in the art. The preparation forms include for example emulsifiable concentrates, dusts, aerosols, wettable powders, granules, oil sprays, heating or non-heating fumigants and powdery or solid agents containing attractants such as baits.

Further, the present compounds may be mixed with other active ingredients to develop more superior insecticidal, acaricidal, nematocidal and/or fungicidal activities.

That is, multi-purpose compositions of excellent efficacy can be produced by mixing the present compounds with active ingredients such as Allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as resmethrin), 3-phenoxybenzyl chrysanthemate, 5-propargylfurfuryl chrysanthemate, 2-methyl-5-propargyl-3-furylmethyl chrysanthemate, d-trans or d-cis.trans isomers of the above chrysanthemates, pyrethrum extracts, d-trans or d-cis.trans chrysanthemic ester of d-allethrolone, 3-phenoxybenzyl 2,2-dimethyl-3-(2,2-dichlorovinyl)cyclopropanecarboxylate, α-cyano-3-phenoxybenzyl 2',2'-dimethyl-3'-(2,2-dichlorovinyl)cyclopropanecarboxylate, α-cyano-3-phenoxybenzyl 2',2',3',3'-tetramethylcyclopropanecarboxylate, α-cyano-3-phenoxybenzyl 2-(4-chlorophenyl)isovalerate, other well-known cyclopropanecarboxylic esters, organo-phosphorus series insecticides such as O,O-dimethyl O-(3-methyl-4-nitrophenyl) phosphorothioate (hereinafter referred to as Fenitrothion), O,O-dimethyl O-4-cyanophenyl phosphorothioate, O,O-dimethyl O-(2,2-dichlorovinyl)phosphate (hereinafter referred to as DDVP), Baycid, vinyphate, Malathion, 2-methoxy-4H-1,3,2-benzoxaphosphorin-2-sulfide, Papthion, Dipterex, Diazinon and the like, carbamate series insecticides such as 1-naphthyl N-methylcarbamate, 3,4-dimethylphenyl N-methylcarbamate, 3-methylphenyl N-methylcarbamate, 2-isopropoxyphenyl N-methylcarbamate, S-methyl N-(methylcarbamoyloxy)thioacetoimidate and the like, N'-(2-methyl-4-chlorophenyl)-N,N-dimethylformamidine, 1,3-bis(carbamoylthio)-2-(N,N-dimethylamino)propane hydrochloride, other insecticides, fungicides, nematocides or acaricides, plant growth regulators, microbial insecticides such as BT, insect hormone compounds, herbicides, other agricultural chemicals and fertilizers. Further, a synergistic effect can be expected by such mixing.

The present insecticidal, acaricidal, nematocidal and/or fungicidal composition may comprise 0.1 to 90% by weight of the above mentioned mixture as the active ingredients.

Next, the synthesis of the present compounds and the insecticidal, acaricidal, nematocidal and/or fungicidal effects of the present compounds will be illustrated with reference to the following examples.

EXAMPLE 1

O,O-dimethyl S-[N-(2,4-dimethylphenyl)-N-ethoxycarbonylmethylcarbamoylmethyl]phosphorodithioate Acetone (150 ml) and the sodium salt (10.8 g) of O,O-dimethyl dithiophosphate were added to a 300-ml four-necked flask, and N-(2,4-dimethylphenyl)-N-ethoxycarbonylmethyl bromoacetamide (16.4 g) was added thereto at room temperature with stirring. After stirring at room temperature for 3 hours, acetone was removed under reduced pressure and water (200 ml) was added thereto. The separated oily substance was extracted with benzene, and the benzene layer was dried over anhydrous sodium sulfate. The solvent was then removed under reduced pressure to obtain 18.4 g of the objective amide phosphorothiolate. $n_D^{24}$ 1.5437.

| Elemental analysis: | C (%) | H (%) | N (%) | S (%) | P (%) |
| --- | --- | --- | --- | --- | --- |
| Calculated (as $C_{16}H_{24}NO_5S_2P$) | 47.40 | 5.97 | 3.45 | 15.82 | 7.64 |
| Found | 47.31 | 6.18 | 3.47 | 15.66 | 7.51 |

EXAMPLE 2

O,O-diethyl S-[N-(2,6-dimethylphenyl)-N-(1-methoxycarbonylethyl)-carbamoylmethyl]phosphorodithioate Acetone (150 ml) and the sodium salt (10.4 g) of O,O-diethyl dithiophosphate were added to a 300-ml four-necked flask, and N-(2,6-dimethylphenyl)-N-(1-methoxycarbonylethyl)chloroacetamide (18.4 g) was added thereto at room temperature with stirring. The reaction mixture was heated under reflux for 3 hours. After cooling, acetone was removed under reduced pressure and water (200 ml) was added thereto. The separated oily substance was extracted with benzene, and the benzene layer was dried over anhydrous sodium sulfate. The solvent was then removed under reduced pressure to obtain 18.8 g of the objective amide phosphorothiolate. $n_D^{23.5}$ 1.5375

| Elemental analysis: | C (%) | H (%) | N (%) | S (%) | P (%) |
| --- | --- | --- | --- | --- | --- |
| Calculated (as $C_{18}H_{28}NO_5S_2P$) | 49.87 | 6.51 | 3.23 | 14.79 | 7.14 |
| Found | 49.65 | 6.39 | 3.11 | 14.96 | 7.02 |

Examples of the compound (I) obtained in the same manner as above will be shown in Table 1, but the present invention is not limited to these examples alone.

TABLE 1

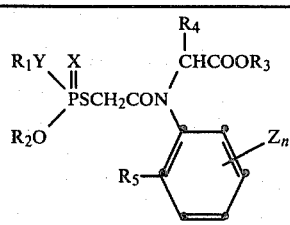

| Compound No. | X Y Physical constant | $R_1$ Elemental analysis | $R_2$ C (%) | $R_3$ H (%) | $R_4$ N (%) | $R_5$ S (%) | $Z_n$ P (%) | Halogen (%) |
|---|---|---|---|---|---|---|---|---|
| 1 | S  O<br>as $C_{16}H_{24}NO_5S_2P$<br>$n_D^{22.5}$ 1.5485 | $CH_3$<br>Cal.<br>F. | $CH_3$<br>47.40<br>47.35 | $C_2H_5$<br>5.97<br>5.77 | H<br>3.45<br>3.16 | $C_2H_5$<br>15.82<br>15.69 | H<br>7.64<br>7.83 | |
| 2 | S  O<br>as $C_{18}H_{28}NO_5S_2P$<br>$n_D^{23}$ 1.5461 | $C_2H_5$<br>Cal.<br>F. | $C_2H_5$<br>49.87<br>49.95 | $C_2H_5$<br>6.51<br>6.38 | H<br>3.23<br>3.00 | $C_2H_5$<br>14.79<br>14.92 | H<br>7.14<br>7.21 | |
| 3 | S  O<br>as $C_{15}H_{22}NO_6S_2P$<br>$n_D^{23}$ 1.5418 | $CH_3$<br>Cal.<br>F. | $CH_3$<br>44.22<br>44.05 | $C_2H_5$<br>5.44<br>5.18 | H<br>3.44<br>3.36 | $CH_3O$<br>15.74<br>15.78 | H<br>7.60<br>7.81 | |
| 4 | S  O<br>as $C_{16}H_{24}NO_6S_2P$<br>$n_D^{22.5}$ 1.5450 | $CH_3$<br>Cal.<br>F. | $CH_3$<br>45.60<br>45.49 | $C_2H_5$<br>5.74<br>5.91 | H<br>3.32<br>3.17 | $C_2H_5O$<br>15.22<br>15.44 | H<br>7.35<br>7.42 | |
| 5 | S  O<br>as $C_{15}H_{21}NO_5S_2PCl$<br>$n_D^{24}$ 1.5474 | $CH_3$<br>Cal.<br>F. | $CH_3$<br>42.30<br>42.11 | $C_2H_5$<br>4.97<br>5.08 | H<br>3.29<br>3.41 | $CH_3$<br>15.06<br>14.96 | 4-Cl<br>7.27<br>7.18 | 8.32(Cl)<br>8.17(Cl) |
| 6 | S  O<br>as $C_{16}H_{24}NO_5S_2P$<br>$n_D^{24}$ 1.5437 | $CH_3$<br>Cal.<br>F. | $CH_3$<br>47.40<br>47.31 | $C_2H_5$<br>5.97<br>6.18 | H<br>3.45<br>3.47 | $CH_3$<br>15.82<br>15.66 | 4-$CH_3$<br>7.64<br>7.51 | |
| 7 | O  S<br>as $C_{19}H_{30}NO_5S_2P$<br>$n_D^{22}$ 1.5295 | n-$C_3H_7$<br>Cal.<br>F. | $C_2H_5$<br>50.99<br>51.05 | $C_2H_5$<br>6.76<br>6.48 | H<br>3.13<br>3.01 | $CH_3$<br>14.33<br>14.52 | 4-$CH_3$<br>6.92<br>6.77 | |
| 8 | S  O<br>as $C_{19}H_{30}NO_5S_2P$<br>$n_D^{24}$ 1.5291 | $CH_3$<br>Cal.<br>F. | $CH_3$<br>50.99<br>50.87 | i-$C_4H_9$<br>6.76<br>6.68 | H<br>3.13<br>3.15 | $C_2H_5$<br>14.33<br>14.51 | 6-$CH_3$<br>6.92<br>6.82 | |
| 9 | S  O<br>as $C_{17}H_{26}NO_5S_2P$<br>$n_D^{24}$ 1.5487 | $CH_3$<br>Cal.<br>F. | $CH_3$<br>48.67<br>48.51 | $C_2H_5$<br>6.25<br>6.54 | H<br>3.34<br>3.18 | $CH_3$<br>15.29<br>15.43 | 4,6-$(CH_3)_2$<br>7.38<br>7.48 | |
| 10 | S  O<br>as $C_{16}H_{24}NO_5S_2P$<br>$n_D^{22}$ 1.5400 | $CH_3$<br>Cal.<br>F. | $CH_3$<br>47.40<br>47.49 | $CH_3$<br>5.97<br>5.69 | $CH_3$<br>3.45<br>3.26 | $CH_3$<br>15.82<br>15.78 | 6-$CH_3$<br>7.64<br>7.69 | |
| 11 | S  O<br>as $C_{18}H_{28}NO_5S_2P$<br>$n_D^{23.5}$ 1.5375 | $C_2H_5$<br>Cal.<br>F. | $C_2H_5$<br>49.87<br>49.65 | $CH_3$<br>6.51<br>6.39 | $CH_3$<br>3.23<br>3.11 | $CH_3$<br>14.79<br>14.96 | 6-$CH_3$<br>7.14<br>7.02 | |
| 12 | S  O<br>as $C_{19}H_{30}NO_5S_2P$<br>$n_D^{24}$ 1.5361 | $C_2H_5$<br>Cal.<br>F. | $C_2H_5$<br>50.99<br>51.17 | $C_2H_5$<br>6.76<br>6.83 | $CH_3$<br>3.13<br>3.01 | $CH_3$<br>14.33<br>14.19 | 6-$CH_3$<br>6.92<br>6.77 | |
| 13 | S  O<br>as $C_{18}H_{28}NO_5S_2P$<br>$n_D^{22.5}$ 1.5350 | $CH_3$<br>Cal.<br>F. | $CH_3$<br>49.87<br>49.69 | $C_2H_5$<br>6.51<br>6.43 | $CH_3$<br>3.23<br>3.00 | n-$C_3H_7$<br>14.79<br>14.87 | H<br>7.14<br>7.40 | |
| 14 | O  O<br>as $C_{18}H_{28}NO_6SP$<br>$n_D^{24}$ 1.5198 | $C_2H_5$<br>Cal.<br>F. | $C_2H_5$<br>51.79<br>52.01 | $CH_3$<br>6.76<br>6.49 | $CH_3$<br>3.36<br>3.25 | $CH_3$<br>7.68<br>7.82 | 6-$CH_3$<br>7.42<br>7.55 | |
| 15 | O  NH<br>as $C_{17}H_{27}N_2O_4S_2P$<br>$n_D^{24}$ 1.5281 | $CH_3$<br>Cal.<br>F. | $C_2H_5$<br>48.79<br>48.92 | $CH_3$<br>6.50<br>6.35 | $CH_3$<br>6.69<br>6.71 | $CH_3$<br>15.32<br>15.39 | 6-$CH_3$<br>7.40<br>7.19 | |
| 16 | O  S<br>as $C_{19}H_{30}NO_5S_2P$<br>$n_D^{22}$ 1.5248 | n-$C_3H_7$<br>Cal.<br>F. | $C_2H_5$<br>50.99<br>51.16 | $CH_3$<br>6.76<br>6.81 | $CH_3$<br>3.13<br>3.05 | $CH_3$<br>14.33<br>14.19 | 6-$CH_3$<br>6.92<br>6.88 | |
| 17 | S  O<br>as $C_{20}H_{32}NO_5S_2P$<br>$n_D^{22}$ 1.5320 | n-$C_3H_7$<br>Cal.<br>F. | n-$C_3H_7$<br>52.04<br>52.30 | $CH_3$<br>6.99<br>6.95 | $CH_3$<br>3.03<br>2.95 | $CH_3$<br>13.89<br>13.81 | 6-$CH_3$<br>6.71<br>6.95 | |
| 18 | S  O<br>as $C_{20}H_{32}NO_5S_2P$<br>$n_D^{22}$ 1.5293 | i-$C_3H_7$<br>Cal.<br>F. | i-$C_3H_7$<br>52.04<br>52.15 | $CH_3$<br>6.99<br>7.13 | $CH_3$<br>3.03<br>3.12 | $CH_3$<br>13.89<br>13.76 | 6-$CH_3$<br>6.71<br>6.58 | |

EXAMPLE 3

The present compounds (1) to (18) were each formulated into a 25% emulsifiable concentrate by mixing 25 parts of the compound, 15 parts of Sorpol SM-200 (a registered trade mark of Tōhō Kagaku Co.) and 60 parts of xylene.

On the bottom of a polyethylene cup of 5.5 cm in diameter was placed a piece of filter paper of the same size, and 0.7 ml of a 500-fold aqueous dilute solution of the emulsifiable concentrate (corresponding to 500 ppm of the active ingredient) was dropped on the filter paper. Sucrose (30 mg) was placed on the paper as bait. Thereafter, 10 female adult houseflies (Musca domestica) were liberated in the cup which was then covered with a lid. After 48 hours, the dead and alive were counted to obtain mortality rates (two replications).

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| $CH_3NHSO_2OCH_2CON\begin{smallmatrix}CH(CH_3)COOCH_3\\ \\CH_3\text{-phenyl}\end{smallmatrix}$* | 0 |
| No treatment | 0 |

*A compound disclosed in Japanese Patent Publication (unexamined) No. 37624/1978.

EXAMPLE 4

The egg mass of rice stem borer (*Chilo suppressalis*) just before hatching was put on rice plants at the tiller stage cultivated in a Wagner's pot (1/10000 are). After 4 days, an aqueous 500-ppm solution prepared in the same manner as in Example 3 was sprayed thereon at a rate of 15 ml/pot. Four days after spraying, the rice stem was cut to count the dead and alive larvae.

| Test compound | Mortality (%) |
|---|---|
| (1) | 95 |
| (4) | 100 |
| (9) | 100 |
| (10) | 93 |
| (11) | 100 |
| (16) | 95 |
| Diazinon | 92 |
| No treatment | 5 |

EXAMPLE 5

Female adult cormine mites (*Tetranychus cinnabarinus*) were made parasitic on the leaves of potted kidney bean, at a rate of 10/leaf, 9 days after sowing, and bred at 27° C. for a week in a constant temperature room. Then, numerous carmine mites were found to be bred at various growth stages. At this time, an aqueous 500-ppm solution prepared in the same manner as in Example 3 was sprayed thereon at a rate of 10 ml/pot by means of a turntable. A week after spraying, the degree of damage of kidney bean and the number of survivals were examined.

| Test compound | Degree of damage* | Number of survivals |
|---|---|---|
| (1) | — | 0 |
| (4) | — | 0 |
| (5) | — | 0 |
| (6) | — | 2 |
| (9) | — | 0 |
| (10) | — | 0 |
| (11) | — | 0 |
| (12) | — | 0 |
| (14) | — | 0 |
| (15) | — | 0 |
| (16) | — | 0 |
| (17) | — | 0 |
| $\begin{smallmatrix}C_2H_5O\\ \phantom{x}\\C_2H_5O\end{smallmatrix}\!\!\!>\!\!\!\underset{\parallel}{\overset{S}{P}}\!\!-\!\!SCH_2CON\!<\!\!\begin{smallmatrix}CH_2COOC_2H_5\\ \\\text{phenyl}\end{smallmatrix}$** | + | 32 |
| PPPS*** | — ~ + | 7 |
| Chlordimeform**** | + | 24 |
| No treatment | + + + | 486 |

*The degree of damage was classified as follows:
—: No damage
+ + +: Same degree of damage as in no treatment
**A compound disclosed in Canadian Patent No. 822,142.
***2-[2-(p-Tert-butylphenoxy)isopropoxy]isopropyl 2-chloroethylsulfite.
****N'—(4-chloro-o-tolyl)-N,N—dimethylformamidine.

EXAMPLE 6

The present compounds (1), (3) and (6) were each formulated into a 40% emulsifiable concentrate and diluted with water so that the content of the compound was 2000 ppm. Ten milliliters of this dilute liquor was placed in a 20-ml beaker with ground stopper, and 0.5 ml of a liquor containing numerous nematodes (*Panagrellus redivivus*) was added thereto. After 48 hours, the dead and alive were examined by means of a binocular microscope.

| Test compound | Judgement* |
|---|---|
| (1) | + + |
| (4) | + + |
| (10) | + + |
| (12) | + + |
| (16) | + + |
| No treatment | — |

*Judgement was made based on the following standard.
—: Mortality less than 50%
+: Mortality 50 to 90%
+ +: Mortality more than 90%

EXAMPLE 7

Preventive effect on downy mildew of cucumber (*Pseudoperonospora cubensis*)

Potted cucumber (var., *Sagami-hanjiro*) at the cotyledonous stage was used as test plant. The aqueous dilute liquor of the emulsifiable concentrate of the present compound was sprayed thereon. After air-drying, the cucumber was inoculated by spraying the spore suspension of *Pseudoperonospora cubensis*. The test plant was infected by placing it in a humid chamber for 24 hours and then cultivating for 5 days at 20° C. under a fluorescent light. The disease severity was expressed by a disease index on the basis of the following standard:

| Disease index | Disease appearance |
| --- | --- |
| 0 | No infected area |
| 1 | One or two infected areas on the cotyledon surface |
| 2 | Infected area of less than 50% of the cotyledon surface |
| 3 | Infected area of 51 to 80% of the cotyledon surface |
| 4 | Infected area of more than 81% of the cotyledon surface |

It was found by this test that the compounds of the present invention have excellent preventive effect.

| Test compound | Concentration of active ingredient (ppm) | Mean value of disease indices |
| --- | --- | --- |
| (2) | 500 | 0 |
| (4) | 500 | 0 |
| (10) | 500 | 0 |
| (11) | 500 | 0 |
| (18) | 500 | 0 |
| 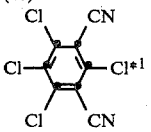 | 500 | 0 |
| No treatment | — | 4 |

*[1] Commercial fungicide

EXAMPLE 8

Curative effect on downy mildew of cucumber (*Pseudoperonospora cubensis*)

Cucumber at the cotyledonous stage was used as test plant in the same manner as in Example 7. The cucumber was inoculated by spraying the spore suspension of *Pseudoperonospora cubensis* and placed for 18 hours in a humid chamber. After air-drying, the aqueous dilute liquor of the emulsifiable concentrate of the present compound was sprayed thereon. The test plant was then infected by cultivating it at 20° C. for 5 days under a fluorescent light. The disease severity was examined in the same manner as in Example 7, and it was found that the present compounds have excellent curative effect.

| Test compound | Concentration of active ingredient (ppm) | Mean value of disease indices |
| --- | --- | --- |
| (11) | 500 | 0 |
| 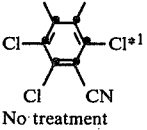 | 500 | 4 |
| No treatment | — | 4 |

*[1] Commercial fungicide

Next, the preparation of the combined insecticide, acaricide, nematocide and fungicide of the present invention will be illustrated with reference to the following preparation examples.

PREPARATION EXAMPLE 1

0.2 Part of each of the present compounds (1) to (18) is dissolved in kerosene and made up to 100 parts with kerosene. Thus, an oil spray of each compound is obtained.

PREPARATION EXAMPLE 2

To 50 parts of each of the present compounds (1) to (18) are added 10 parts of Sorpol SM-200 (a registered trade mark of Toho Kagaku Co.) and 40 parts of xylene, and the mixture is well stirred to make a solution. Thus, an emulsifiable concentrate of each compound is obtained.

PREPARATION EXAMPLE 3

Twenty parts of the present compound (10) and 20 parts of Fenitrothion (described above) are dissolved in 50 parts of xylene. Ten parts of Sorpol SM-200 (described above) is added, and the mixture is well stirred to make a solution. Thus, an emulsifiable concentrate containing the compounds is obtained.

Multi-purpose mixed emulsifiable concentrates are also obtained using insecticides, acaricides, nematocides or fungicides other than Fenitrothion.

PREPARATION EXAMPLE 4

0.1 Part of the present compound (12), 0.2 part of tetramethrin, 7 parts of xylene and 7.7 parts of deodorized kerosene are well mixed to make a solution. The solution is filled in an aerosol container. After attaching a valve portion to the container, 85 parts of a propellant (liquefied petroleum gas) is charged therein under pressure through the valve. Thus, an aerosol containing the compounds is obtained.

PREPARATION EXAMPLE 5

Fourty parts of each of the present compounds (1) to (18) and 5 parts of Sorpol SM-200 (described above) are well mixed, and 55 parts of 300-mesh diatomaceous earth is added thereto. The mixture is then well mixed while being stirred in a mortar. Thus, a wettable powder of each compound is obtained.

PREPARATION EXAMPLE 6

Three parts of each of the present compounds (1) to (18) is dissolved in 20 parts of acetone, and 97 parts of 300-mesh talc is added thereto. The mixture is well mixed with stirring, and then acetone is removed by evaporation. Thus, a dust of each compound is obtained.

PREPARATION EXAMPLE 7

A mixture of 1 part of each of the present compounds (11) and (14) and 2 parts of 3-methylphenyl N-methylcarbamate is dissolved in 20 parts of acetone, and 97 parts of 300-mesh talc is added thereto. The mixture is well mixed while being stirred in a mortar, and acetone is then removed by evaporation. Thus, a dust containing the compounds is obtained.

PREPARATION EXAMPLE 8

To 5 parts of each of the present compounds (1) and (18) are added 5 parts of Toyolignin CT (a registered trade mark of Toyo Spinning Co.) and 90 parts of GSM Clay (a registered trade mark of Zieklite Mining Co.), and the mixture is well mixed while being stirred in a mortar.

PREPARATION EXAMPLE 9

To 80 parts of each of the present compounds (1) to (18) are added 5 parts of Sorpol SM-200 (a registered trade mark of Toho Kagaku Co.) and 15 parts of xylene, and the mixture is well stirred to make a solution. Thus, an emulsifiable concentrate of each compound is obtained.

Thereafter, the mixture is well mixed with water in an amount of 10% by weight based thereon, granulated by means of a granulator and air-dried. Thus, granules of each compound are obtained.

What is claimed is:

1. A compound of the formula

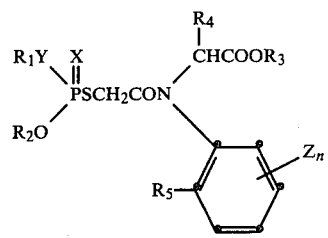

wherein X is an oxygen or sulfur atom, Y is an oxygen or sulfur atom or imino group, $R_1$ and $R_2$, which may be the same or different, are each a $C_1$–$C_3$ alkyl group, $R_3$ is a $C_1$–$C_4$ alkyl group, $R_4$ is a hydrogen atom or methyl group, $R_5$ is a $C_1$–$C_3$ alkyl, methoxy or ethoxy group, Z is a hydrogen atom, a methyl group or chlorine atom and n is 1 or 2.

2. A compound according to claim 1, wherein X is a sulfur atom, $R_1$, $R_2$ and $R_3$, which may be the same or different, are each a $C_1$–$C_3$ alkyl group, $R_4$ is a hydrogen atom or methyl group, $R_5$ is a $C_1$–$C_3$ alkyl, methoxy or ethoxy group, Z is a methyl group or chlorine atom in the ortho-position on the phenyl ring, and n is 1.

3. A compound according to claim 1, wherein X is a sulfur atom, $R_1$, $R_2$ and $R_3$, which may be the same or different, are each a $C_1$–$C_3$ alkyl group, $R_4$ is a hydrogen atom or methyl group, $R_5$ is a $C_1$–$C_3$ alkyl, methoxy or ethoxy group, Z is a methyl group or chlorine atom, and n is 1 or 2, with the proviso that there is a Z group in the ortho-position on the phenyl ring.

4. A compound according to claim 1, wherein X is a sulfur atom, Y is an oxygen atom, $R_1$ and $R_2$, which may be the same or different, are each a methyl or ethyl group, $R_3$ is a methyl or ethyl group, $R_4$ is a hydrogen atom or methyl group, $R_5$ is a methyl, ethyl, methoxy or ethoxy group, Z is a hydrogen atom or a methyl group and n is 1 or 2.

5. The compound according to claim 1, which is

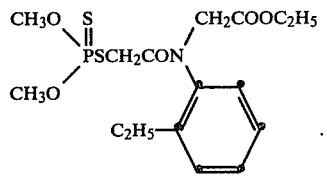

6. The compound according to claim 1, which is

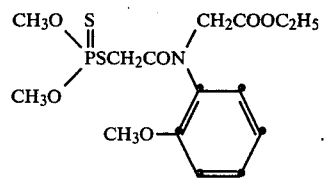

7. The comound according to claim 1, which is

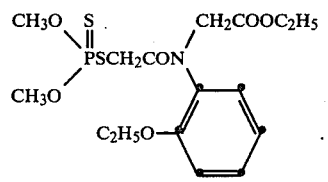

8. The compound according to claim 1, which is

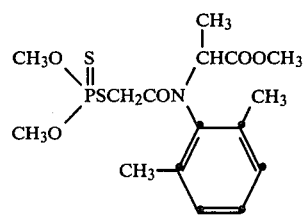

9. The compound according to claim 1, which is

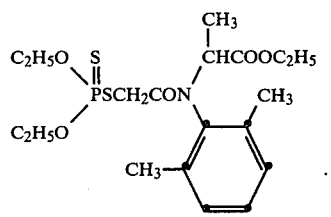

10. A method for controlling insects, mites, nematodes and/or fungi which comprises contacting the insects, mites, nematodes and/or fungi with an insecticidally, miticidally, nematocidally and/or fungicidally effective amount of at least one amide phosphorothiolate derivative as defined in claim 1.

11. A method for controlling rice stem borers, houseflies and mites which comprises contacting the rice stem borers, houseflies and mites with an insecticidally and miticidally effective amount of at least one amide phosphorothiolate derivative as defined in claim 1.

12. A method for controlling diseases caused by Phycomycetes which comprises contacting the Phycomycetes with a fungicidally effective amount of at least one amide phosphorothiolate derivative as defined in claim 1.

13. An insecticidal, acaricidal, nematocidal and/or fungicidal composition comprising an inert carrier or diluent and at least one amide phosphorothiolate derivative as defined in claim 1 as an active ingredient in an insecticidally, acaricidally, nematocidally and/or fungicidally effective amount.

* * * * *